US007758274B2

(12) United States Patent
Paul

(10) Patent No.: US 7,758,274 B2

(45) Date of Patent: Jul. 20, 2010

(54) QUICK ATTACHMENT APPARATUS FOR USE IN ASSOCIATION WITH ORTHOPEDIC INSTRUMENTATION AND TOOLS

(75) Inventor: Marc T. Paul, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 524 days.

(21) Appl. No.: 11/402,524

(22) Filed: Apr. 11, 2006

(65) Prior Publication Data

US 2007/0266529 A1 Nov. 22, 2007

(51) Int. Cl.
*F16B 7/10* (2006.01)

(52) U.S. Cl. .................................... 403/109.3; 403/104

(58) Field of Classification Search ................. 403/104, 403/105, 107, 109.3, 109.4, 120, 206, 325; 285/34, 308, 317, 902; 248/408, 409, 412; 411/433; 74/424.72, 424.78, 424.95; 269/181
See application file for complete search history.

(56) References Cited

U.S. PATENT DOCUMENTS

| | | | | |
|---|---|---|---|---|
| 150,900 | A * | 5/1874 | Silver | 269/182 |
| 825,151 | A * | 7/1906 | McLean | 269/181 |
| 906,135 | A * | 12/1908 | Hilton | 285/34 |
| 1,071,921 | A * | 9/1913 | Hilton | 285/34 |
| 1,312,942 | A * | 8/1919 | Anderson | 74/424.78 |
| 1,612,124 | A * | 12/1926 | Huelsick | 254/98 |
| 2,218,319 | A * | 10/1940 | Pfauser | |
| 2,463,179 | A * | 3/1949 | Iftiger, Sr. | 285/34 |
| 2,644,498 | A * | 7/1953 | Malecki | |
| 2,671,482 | A * | 3/1954 | Gordon | |
| 3,071,188 | A * | 1/1963 | Raulins | 285/906 |
| 3,220,721 | A * | 11/1965 | Wahli et al. | |
| 3,570,836 | A * | 3/1971 | Pettavel | |
| 4,048,897 | A * | 9/1977 | Price, Jr. | |
| 4,172,606 | A * | 10/1979 | Howe | 285/34 |
| 4,269,331 | A * | 5/1981 | Watson | 74/424.78 |
| 4,295,389 | A * | 10/1981 | Geisthoff et al. | 403/107 |
| 4,693,656 | A * | 9/1987 | Guthrie | |
| 5,090,747 | A * | 2/1992 | Kotake | 285/317 |
| 5,139,276 | A * | 8/1992 | Balsells | |
| 5,195,803 | A * | 3/1993 | Quintile | 403/109.7 |
| 5,326,076 | A * | 7/1994 | Sorensen et al. | |
| 5,770,812 | A * | 6/1998 | Kitayama | |
| 5,898,974 | A * | 5/1999 | Boyer | 403/296 |

(Continued)

FOREIGN PATENT DOCUMENTS

DE 2731525 A1 * 1/1978

(Continued)

*Primary Examiner*—Victor MacArthur

(57) ABSTRACT

A quick attachment apparatus for use in association with orthopedic instrumentation and/or tools for releasable connection to a device, including a coupling member defining a passage extending generally along a longitudinal axis and sized to slidably receive a connection portion of the device, a locking member transitionable between a locked position and an unlocked position, a biasing member engaged between the coupling member and the locking member to bias the locking member into engagement against the connection portion to substantially prevent relative axial movement between the coupling member and the connection portion, and wherein application of a lateral force onto the locking member results in displacement of the coupling member generally along a transverse axis wherein the locking member is disengaged from the connection portion to allow relative axial movement between the coupling member and the connection portion.

16 Claims, 5 Drawing Sheets

U.S. PATENT DOCUMENTS

| | | | |
|---|---|---|---|
| 5,911,215 | A * | 6/1999 | Fisher, Jr. |
| 6,789,986 | B2 * | 9/2004 | Story, Jr. |
| 7,207,971 | B2 * | 4/2007 | Hart et al. |
| 2004/0122361 | A1 * | 6/2004 | Hart et al. |

FOREIGN PATENT DOCUMENTS

| | | | |
|---|---|---|---|
| FR | 2429370 | A * | 2/1980 |
| GB | 597381 | * | 1/1948 |
| GB | 781248 | * | 8/1957 |

* cited by examiner

QUICK ATTACHMENT APPARATUS FOR USE IN ASSOCIATION WITH ORTHOPEDIC INSTRUMENTATION AND TOOLS

FIELD OF THE INVENTION

The present invention generally relates to medical and surgical devices, and more particularly relates to a quick attachment apparatus for use in association with various types of orthopedic instrumentation and tools that allows one or more structures to be quickly and adjustably attached to and/or detached from other structures.

BACKGROUND

Various types of instrumentation and tools are used to perform a multitude of medical and surgical procedures. For example, orthopedic instrumentation and devices commonly require that one or more structures be attached to and/or detached from adjacent structures via a connector or coupler mechanism. With regard to surgical tools, it is commonly required that a first tool portion be attached to and/or detached from a second tool portion. In some instances, such interconnections must be accomplished quickly and precisely. Additionally, in some cases, the interconnection must be adjustable as well.

Thus, there remains a need for a quick attachment apparatus for use in association with various types of orthopedic instrumentation and tools that allows one or more structures to be quickly and adjustably attached to and/or detached from other structures. The present invention satisfies this need and provides other benefits and advantages in a novel and unobvious manner.

SUMMARY

The present invention relates to a quick attachment apparatus for use in association with various types of orthopedic instrumentation and tools that allows one or more structures to be quickly and adjustably attached to and/or detached from other structures. While the actual nature of the invention covered herein can only be determined with reference to the claims appended hereto, certain forms of the invention that are characteristic of the preferred embodiments disclosed herein are described briefly as follows.

In one form of the invention, a quick attachment apparatus is provided for use in association with orthopedic instrumentation and/or tools for releasable connection to a device, the apparatus including a coupling member defining a passage extending generally along a longitudinal axis and sized to receive a connection portion of the device, a locking member associated with the coupling member and being transitionable between a locked position and an unlocked position, a biasing member engaged between the coupling member and the locking member to bias the locking member toward the locked position wherein the locking member is engaged with the connection portion to substantially prevent relative axial displacement between the coupling member and the connection portion, and wherein application of a lateral force onto the locking member results in displacement of the locking member generally along a transverse axis to transition the locking member to the unlocked position wherein the locking member is disengaged from the connection portion to allow relative axial displacement between the coupling member and the connection portion.

In another form of the invention, a quick attachment apparatus is provided for use in association with orthopedic instrumentation and/or tools for releasable connection to a device, the apparatus including a coupling member defining a passage extending generally along a longitudinal axis and defining a first threading, a locking member associated with the coupling member and defining a second threading engagable with the first threading and being transitionable between a locked position and an unlocked position, wherein the first threading is disengaged from the second threading when the locking member is positioned in the unlocked position to allow variable adjustment of the connection portion to a select axial position relative to the coupling member, and wherein the first threading is engaged with the second threading when the locking member is positioned in the locked position to lock the connection portion in the select axial position relative to the coupling member, and wherein rotational displacement of the connection portion relative to the coupling member threadingly engages the first threading with the second threading to provide relatively finer variable adjustment to the select axial position of the connection portion relative to the coupling member.

In a further form of the invention, a quick attachment apparatus is provided for use in association with orthopedic instrumentation and/or tools for releasable connection to a device, the apparatus including a coupling member defining a passage extending generally along a longitudinal axis and sized to receive a connection portion of the device, a locking member associated with the coupling member and being transitionable between a locked position and an unlocked position, means for variably adjusting the connection portion to a select axial position relative to the coupling member, means for transitioning the locking member to the locked position to lock the connection portion in the select axial position relative to the coupling member, and means for finely adjusting the select axial position of the connection portion relative to the coupling member.

It is one object of the present invention to provide a quick attachment apparatus that allows one or more structures to be quickly and adjustably attached to and/or detached from various types of orthopedic devices or instruments. Further objects, features, advantages, benefits, and aspects of the present invention will become apparent from the drawings and description contained herein.

DESCRIPTION OF THE ILLUSTRATED EMBODIMENTS

Figure 1:
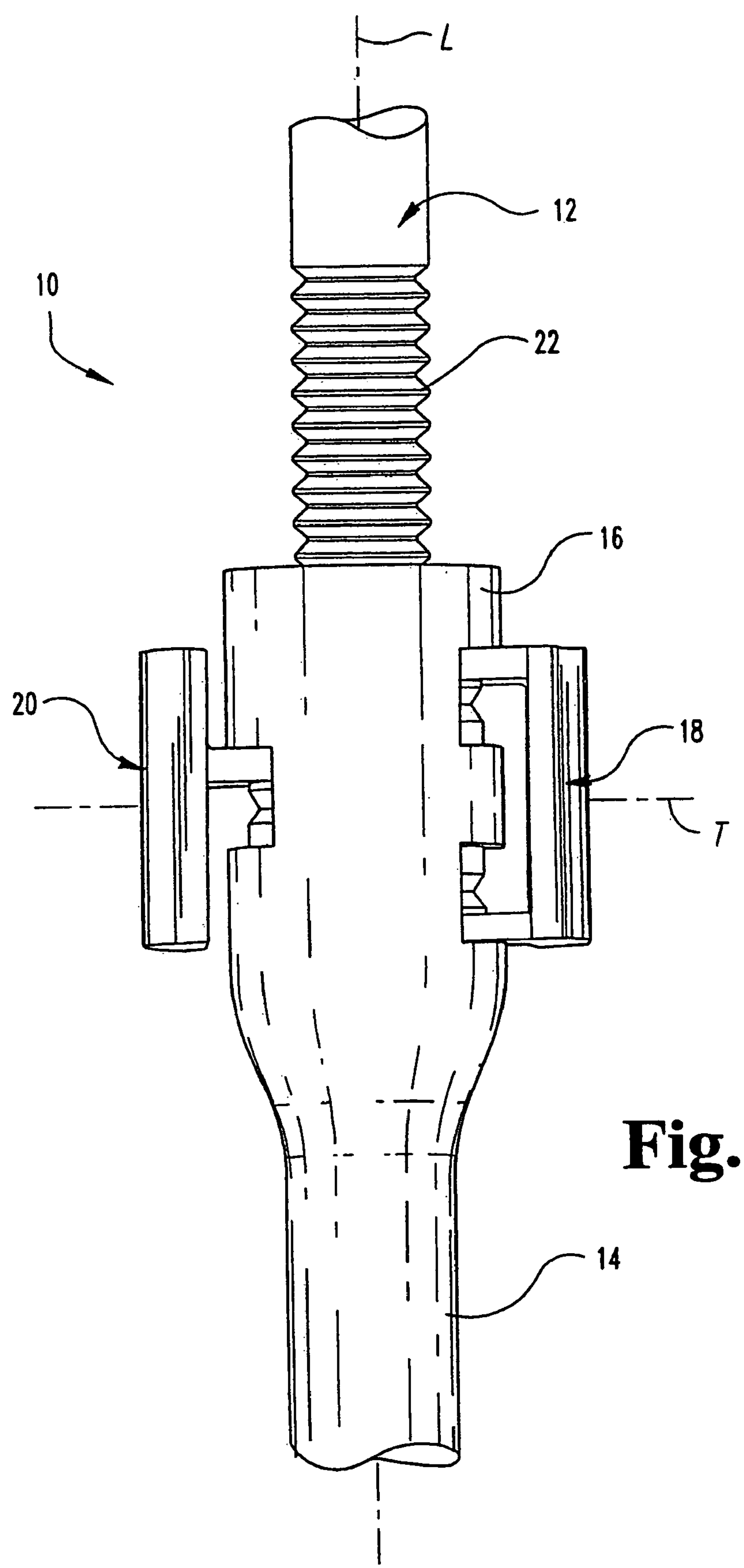
FIG. 1 illustrates a quick attachment apparatus according to one form of the present invention, as attached to an adjacent device.

Referring to FIG. 1, illustrated therein is a quick attachment device 10 according to one form of the present invention for connection with a surgical instrument or device 12. The quick attachment device 10 may be incorporated into the design of various types of surgical instruments or tools to allow two or more structures to be quickly and adjustably interconnected to one another.

In one embodiment, the quick attachment device 10 extends generally along a longitudinal axis L and includes a coupling member 14 having a coupling portion 16 that is configured to selectively engage and disengage a connection portion 22 associated with the surgical device 12. The quick attachment device 10 also includes one or more locking members 18, 20 for releasably engaging and/or disengaging the quick attachment device 10 to/from the surgical device 12. In the illustrated embodiment, the coupling portion 16 of the attachment device 10 and the connection portion 22 of the surgical device 12 are positioned in axial alignment with one another generally along the longitudinal axis L. However, it should be understood that other positions and orientations of the coupling portion 16 relative to the connection portion 22 are also contemplated as falling within the scope of the present invention.

In one embodiment, the quick attachment device 10 is biased toward a locked or engaged state (FIG. 2), with the locking members 18, 20 engaged with the connection portion 22 of the surgical device 12 so as to substantially prevent or prohibit relative movement therebetween, which in turn substantially prevents or prohibits relative movement between the attachment device 10 and the surgical device 12. In one embodiment, the locking members 18, 20 include a pair of manual push tabs which are preferably, but not necessarily, located on opposite sides of the coupling portion 16 of the attachment device 10. In the illustrated embodiment, the attachment device 10 includes a pair of locking members 18, 20. However, it should be understood that other embodiments are also contemplated wherein the attachment apparatus includes a single locking member or three or more locking members.

In one embodiment, manual engagement of the push tabs selectively transitions the quick attachment device 10 from the locked or engaged state (FIG. 2) toward an unlocked or disengaged state (FIG. 3), with the locking members 18, 20 disengaging the connection portion 22 of the surgical device 12 so as to allow relative movement therebetween, which in turn allows relative movement between the attachment device 10 and the surgical device 12. In one embodiment, manual application of a lateral force F onto the push tabs generally along a transverse axis T causes the attachment device 10 to transition toward the unlocked or disengaged state (FIG. 3) to selectively release the connection portion 22 of the surgical device 12, which in turn allows the surgical device 12 to be variably adjusted relative to and/or removed from the quick attachment device 10. As indicated above, the locking members 18, 20 are preferably biased such that release of the lateral force F causes the attachment device 10 to transition back toward the locked or engaged state (FIG. 2) to once again engage the locking members 18, 20 with the connection portion 22 so as to substantially prevent or prohibit relative movement between the attachment device 10 and the surgical device 12.

Figure 2:
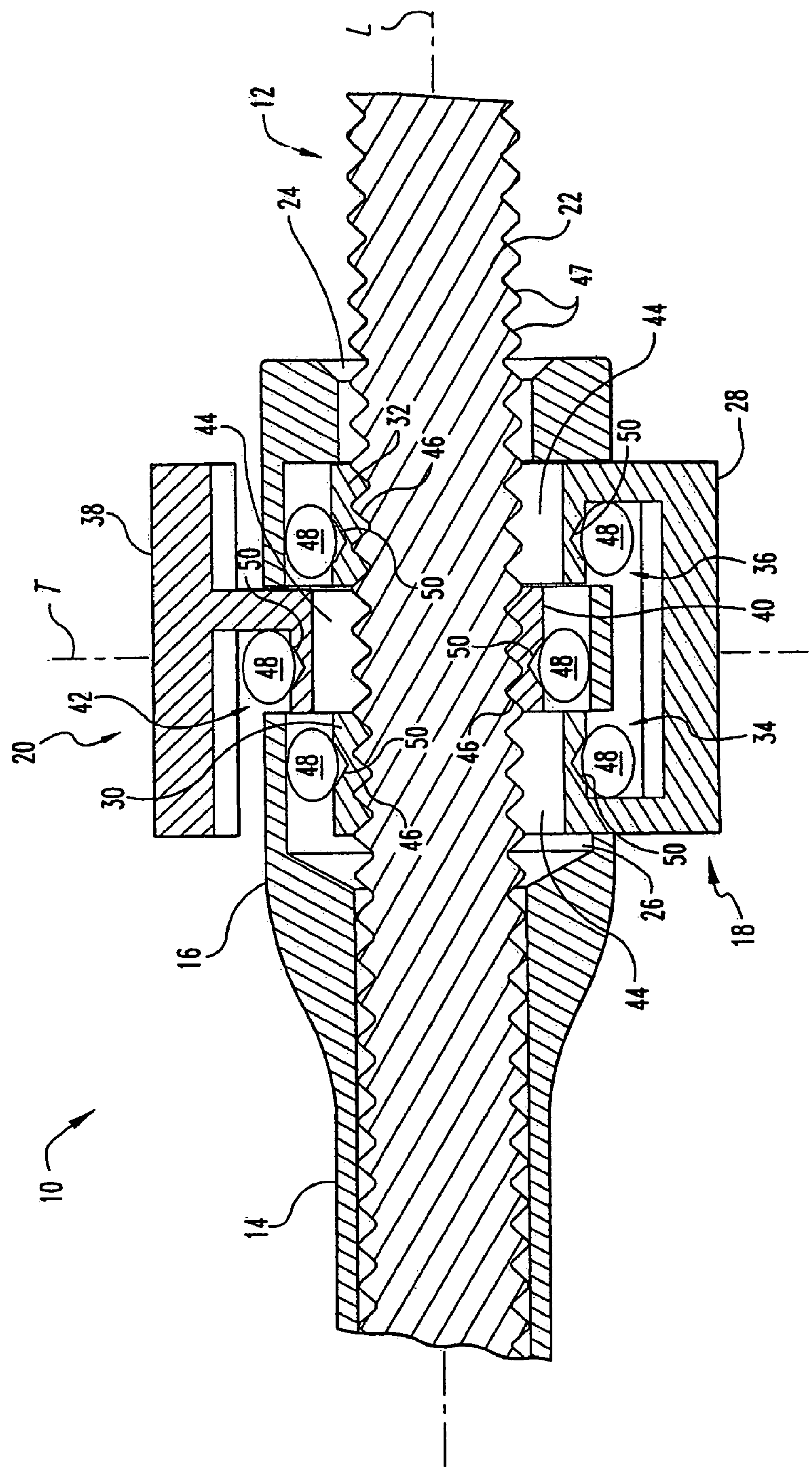
FIG. 2 is a partial cross-sectional view of a portion of the quick attachment apparatus illustrated in FIG. 1 with the biasing members shown schematically, as shown in a locked or engaged state.

Referring to FIG. 2, illustrated therein is a cross-sectional view of a portion of the quick attachment device 10, as shown in the locked or engaged state. In the illustrated embodiment, the coupling portion 16 of the attachment device 10 includes a passage 24 extending generally along the longitudinal axis L so as to define a receiver portion, with the connection portion 22 being configured as an axially-extending shaft portion. In one embodiment, the axial passage 24 has an inner cross section sized and shaped somewhat larger than the outer cross section of the shaft portion 22 such that the shaft portion 22 may displaced within the passage 24. The axial passage 24 further defines a cavity or recess 26 that is sized and shaped to contain or house portions of the first and second locking members 18, 20 therein. Additionally, the distal end portion of the passage 24 may be tapered to facilitate initial insertion of the shaft portion 22 within the passage 24. As should be appreciated, the shaft portion 22 may be axially displaced within the passage 24 when a lateral force F is applied to the locking members 18, 20 to selectively transition the quick attachment device 10 toward the unlocked or disengaged state. In one embodiment, the shaft portion 22 and the passage 24 each have a generally circular configuration. However, other shapes and configurations of the shaft portion 22 and the passage 24 are also contemplated as falling within the scope of the present invention.

Figure 4:
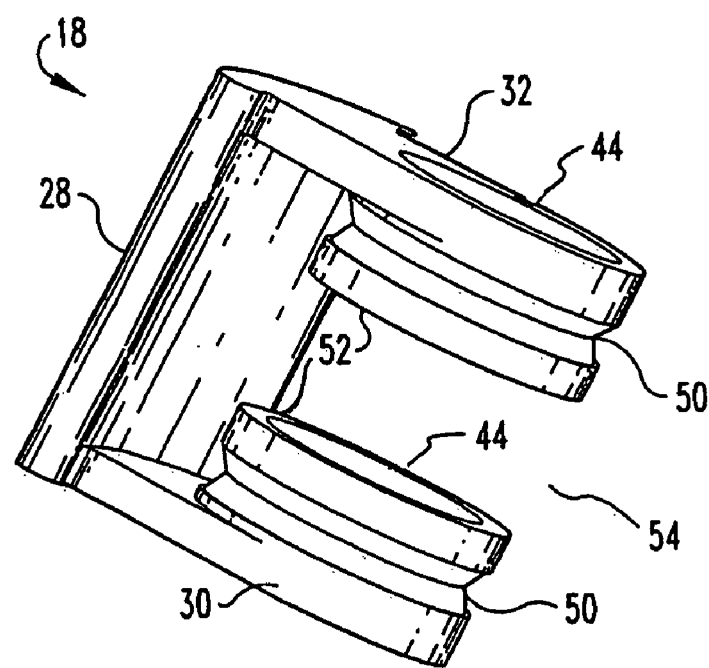
FIG. 4 is a perspective view of a first portion of a push tab locking member according to one embodiment of the present invention for use in association with the quick attachment apparatus illustrated in FIGS. 1-3.

As illustrated in FIG. 4, in one embodiment, the first locking member 18 includes a first push tab 28, a first securing member 30 and a second securing member 32. An oblong or oval-shaped slot 44 is defined axially through each of the first and second securing members 30 and 32, with one or more engagement elements 46 (FIG. 2) formed along an inner surface of the slots 44. The slots 44 are each sized and shaped to receive the connection portion 22 of the surgical device 12 therein. In one embodiment, the securing members 30, 32 include axial protrusions 52 extending toward one another, with an axial space or gap 54 defined between the protrusions 52, and with a groove or recess 50 formed about an outer surface of each of the protrusions 52.

As shown in FIG. 2, the first push tab 28 protrudes outwardly through a pair of openings 34, 36 extending laterally though the receiver portion 16 and communicating with the axial passage 24. The first and second securing members 30, 32 are located within the cavity 26 and are positioned laterally adjacent the connection portion 22 of the surgical device 12. The oblong slots 44 in the securing members 30, 32 allow the locking member 18 to be displaced relative to the connection portion 22 generally along the transverse axis T when a lateral force F is applied to the push tab 28, thereby releasing the engagement elements 46 of the securing members 30, 32 from the connection portion 22 of the surgical device 12.

Figure 5:
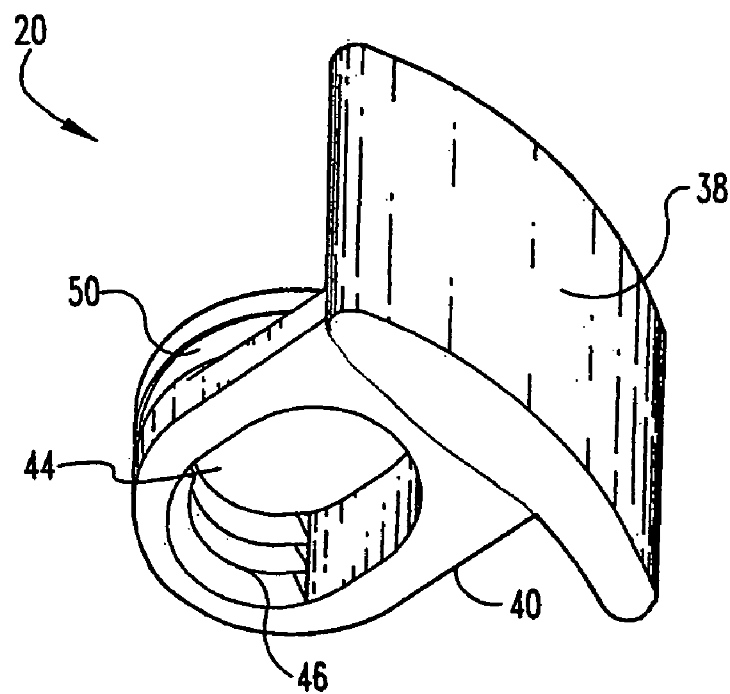
FIG. 5 is a perspective view of a second portion of a push tab locking member according to one embodiment of the present invention for use in association with the quick attachment apparatus illustrated in FIGS. 1-3.

As illustrated in FIG. 5, in one embodiment, the second locking member 20 includes a second push tab 38 and a third securing member 40. An oblong or oval-shaped slot 44 is defined axially through the third securing member 40, with one or more engagement elements 46 formed along an inner surface of the slot 44. The slot 44 is sized and shaped to receive the connection portion 22 of the surgical device 12 therein. In one embodiment, the securing member 40 comprises an axial protrusion, with a groove or recess 50 formed about an outer surface of the protrusion.

As shown in FIG. 2, the second push tab 38 protrudes outwardly through an opening 42 extending laterally though the receiver portion 16 and communicating with the axial passage 24. The third securing member 40 is located within the cavity 26 and is positioned laterally adjacent the connection portion 22 of the surgical device 12. In the illustrated embodiment, the third securing member 40 is positioned within the space or gap 54 between the first and second securing members 30, 32 of the first locking member 18, with the slot 44 in the securing member 40 generally aligned with the slots 44 in the securing members 30, 32. The oblong slots 44 in the securing member 40 allows the locking member 20 to be displaced relative to the connection portion 22 generally along the transverse axis T when a lateral force F is applied to the push tab 38, thereby releasing the engagement elements 46 of the securing member 40 from the connection portion 22 of the surgical device 12.

As indicated above, an inside surface of each of the securing members 30, 32, 40 includes at least one engagement element 46. Additionally, the connection portion 22 of the surgical device 12 includes a number of engagement elements 47 that are configured to correspondingly engage the engagement elements 46. In the illustrated embodiment, when the quick attachment device 10 is placed in the locked or engaged position, the engagement elements 46 of the securing members 30, 32, 40 mate or interdigitate with the engagement elements 47 formed along the connection portion 22 to correspondingly lock the connection portion 22 in a select axial position so as to substantially prevent or prohibit axial displacement of the surgical device 12 relative to the attachment device 10.

In one embodiment, the engagement elements 46 associated with the securing members 30, 32, 40 comprise internal thread segments, and the engagement elements 47 associated with the connection portion 22 comprise external threads which mate with the internal thread segments 46. However, other configurations of engagement elements are also contemplated as falling within the scope of the present invention, including various types of lateral projections and lateral recesses or grooves associated with the locking members 18, 20 and the connection portion 22. In one alternative embodiment, the engagement elements 46, 47 may comprise ratcheting elements. In other embodiments, the engagement elements 46, 47 may comprise a number of pins or other projections that are selectively positioned within corresponding apertures or openings. Other suitable alternative embodiments are also contemplated as falling within the scope of the present invention. Although specific configurations and arrangements of the locking members 18, 20 and the connection portion 22 have been illustrated and described herein, it should be understood that other configurations and arrangements are also contemplated as falling within the scope of the present invention.

As indicated above, the locking members 18, 20 are preferably biased toward the locked or engaged position of the attachment device 10. In one embodiment, one or more biasing members 48 are positioned between the securing members 30, 32, 40 and the coupling portion 16. In the illustrated embodiment, the biasing members 48 are positioned between an outwardly facing surface of the securing members 30, 32, 40 (opposite the engagement elements 46) and an inside surface of the coupling portion 16. The biasing members 48 operate to bias or force the engagement elements 46 of the securing members 30, 32, 40 into secure engagement with the engagement elements 47 of the connection portion 22, thereby fixedly securing the attachment device 10 to the surgical device 12. When a lateral force F is applied to the locking members 18, 20, the biasing members 48 are compressed, and such compressive forces operate to once again bias the elements 46 into engagement with the elements 47 when the lateral force F is released.

Figure 6:
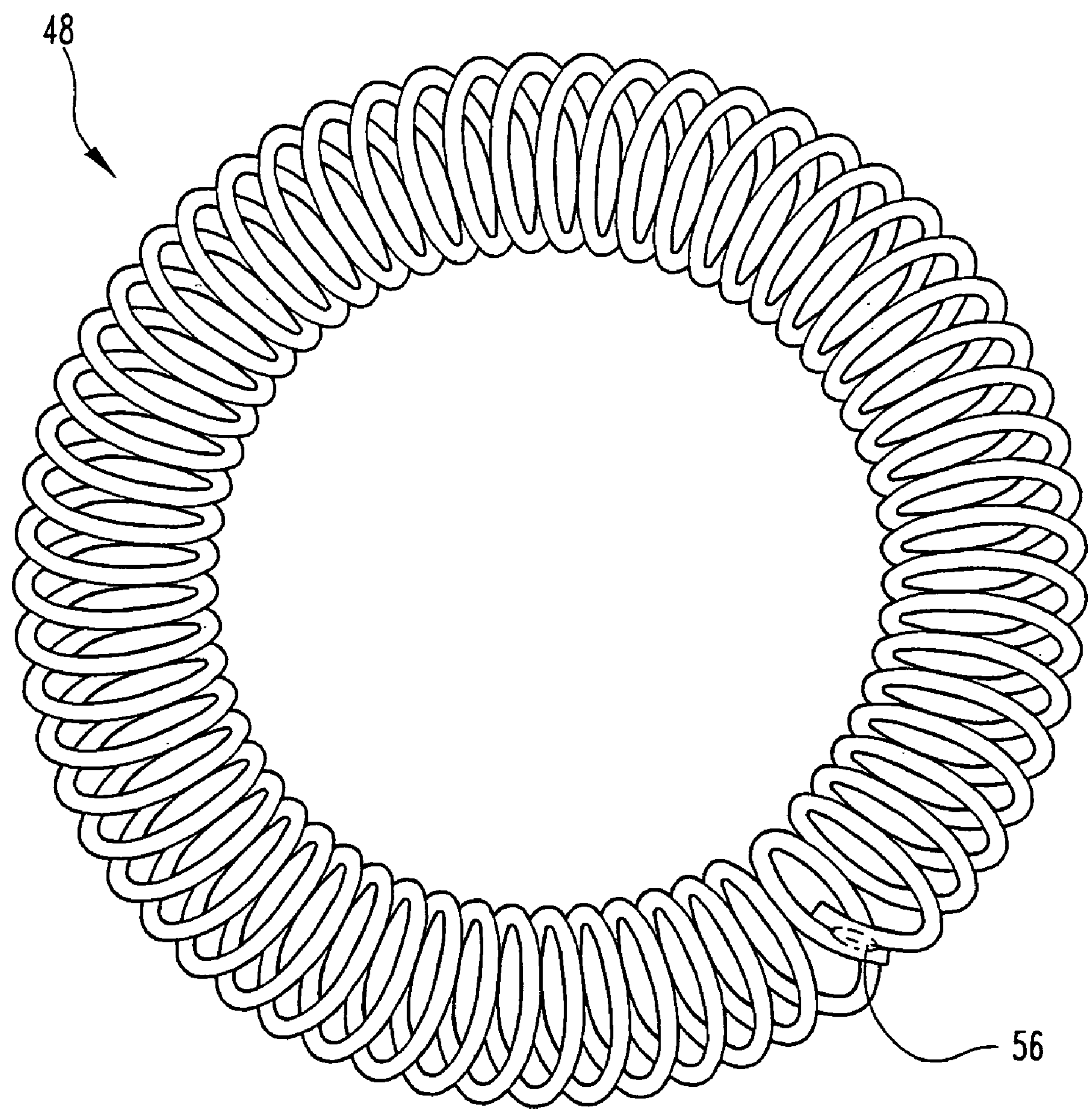
FIG. 6 illustrates a biasing mechanism according to one embodiment of the present invention for use in association with the quick attachment apparatus illustrated in FIGS. 1-3.

Referring to FIG. 6, in one embodiment, the biasing members 48 comprise springs, and more specifically canted coil springs. In the illustrated embodiment, the canted coil springs 48 each comprise a round wire spring defining inclining elliptical coils that deflect independently when compressed. Cut ends 56 of the spring 48 may be welded together to form a continuous annular ring. The springs 48 are preferably held in a generally stationary axial position relative to the locking members 18, 20 via placement within the grooves or recesses 50 formed about each of the securing members 30, 32, 40. Although a specific configuration of the biasing member 48 has been illustrated and described herein, it should be understood that other types and configurations of biasing members are also contemplated as falling within the scope of the present invention, including other types and configurations of springs.

Figure 3:
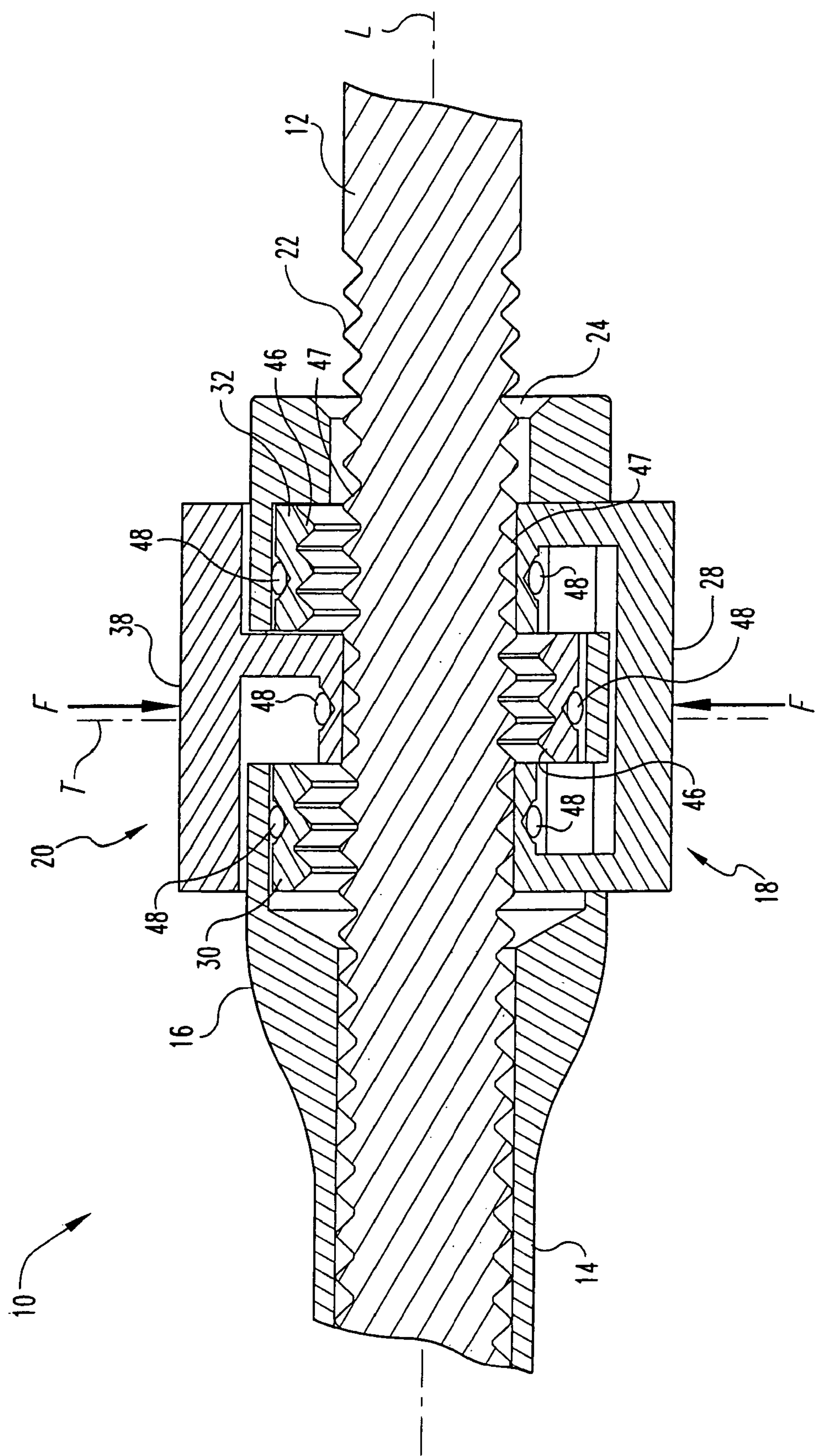
FIG. 3 is a partial cross-sectional view of a portion of the quick attachment apparatus illustrated in FIG. 1 with the biasing members shown schematically, as shown in an unlocked or disengaged state.

Referring to FIG. 3, illustrated therein is a cross-sectional view of a portion of the quick attachment device 10, as shown in an unlocked or released position. Notably, when lateral forces F are applied to the push tabs 28, 38 of the locking members 18, 20, the engagement elements 46 defined by the securing members 30, 32, 40 are released from the engagement elements 47 defined by the connection portion 22. As such, the surgeon or technician may freely adjust the axial position of the surgical device 12 relative to the attachment device 10. During application of the lateral forces F, the springs 48 are transitioned to a retracted or compressed state, thereby biasing the locking members 18, 20 back toward the locked or engaged state shown in FIG. 2 when the lateral forces F are released from the push tabs 28, 38.

Once the attachment device 10 is transitioned back to the locked or engaged position, with the thread segments 46 defined by the locking members 18, 20 matingly engaged with the external threads 47 formed along the connection portion 22, the axial position of the connection portion 22 may be further adjusted relative to the attachment device 10 via application of a rotational force onto the attachment device 10 and/or the surgical device 12. As should be appreciated, the coupling portion 16 is capable of being released from the connection portion 22 to provide a relatively large degree of adjustment to the axial position of the attachment device 10 relative to the surgical device 12, and is also capable of providing a relatively finer degree of adjustment to the axial position upon re-engagement of the attachment device 10 with the surgical device 12 via threading engagement between the locking members 18, 20 and the connection portion 22.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A quick attachment apparatus for use in association with orthopedic instrumentation or tools, comprising:

a connection portion of a device;

a coupling member defining a passage extending generally along a longitudinal axis and having an inner cross section sized to receive said connection portion of the device, said inner cross section of said passage including an inside surface;

a locking member associated with said coupling member, said locking member including first and second locking elements, each of said locking elements including a portion contained within said passage in said coupling member, said locking elements transitionable between a locked position and an unlocked position;

a first biasing member engaged between said inside surface of said passage in said coupling member and said portion of said first locking element within said passage to bias said first locking element toward said locked position, and a second biasing member engaged between said inside surface of said passage in said coupling member and said portion of said second locking element within said passage to bias said second locking element toward said locked position, and wherein said locking elements are engaged with said connection portion to substantially prevent relative axial displacement between said coupling member and said connection portion; and wherein said first and second biasing members are positioned within a gap between said coupling member and said locking elements, wherein said first and second biasing members are configured to exert a compression force onto said locking elements to bias said locking elements into engagement with said connection portion, and wherein each of said first and second biasing members comprises a spring; and wherein said locking elements are transitionable from said locked position to said unlocked position by application of lateral forces onto said locking elements which results in displacement of said locking elements generally along a transverse axis to transition said locking elements to said unlocked position wherein said locking elements are disengaged from said connection portion to allow relative axial displacement between said coupling member and said connection portion; and wherein said first and second locking elements are displaceable in opposite directions along said transverse axis upon application of said lateral forces to transition said locking elements toward said unlocked position, and wherein said locking elements and said connection portion define engagement elements that cooperate with one another to substantially prevent said relative axial displacement between said coupling member and said connection portion; and wherein said connection portion defines at least one of said engagement elements along a length of said connection portion, each of said first and second locking elements including at least one of said engagement elements, said at least one of said engagement elements defined by said locking elements engaged with said at least one of said engagement elements defined by said connection portion when said locking elements are in said locked position to secure said connection member in a select axial position relative to said coupling member; and wherein said spring exerts said compression force onto said corresponding one of said locking elements to bias said corresponding one of said locking elements toward said locked position; and wherein said spring includes end portions that are interconnected with one another to define an annular ring extending about at least a portion of said corresponding one of said locking elements.

2. The quick attachment apparatus of claim 1, wherein said spring comprises a canted coil spring.

3. A quick attachment apparatus for use in association with orthopedic instrumentation or tools, comprising:

a connection portion of a device;

a coupling member defining a passage extending generally along a longitudinal axis and sized to receive said connection portion of the device;

a locking member associated with said coupling member, said locking member including first and second locking elements, said locking elements transitionable between a locked position and an unlocked position;

a first biasing member engaged with said first locking element to bias said first locking element toward said locked position, and a second biasing member engaged with said second locking element to bias said second locking element toward said locked position, and wherein said locking elements are engaged with said connection portion to substantially prevent relative axial displacement between said coupling member and said connection portion; and wherein said locking elements are transitionable from said locked position to said unlocked position by application of lateral forces onto said locking elements which results in displacement of said locking elements generally along a transverse axis to transition said locking elements to said unlocked position wherein said locking elements are disengaged from said connection portion to allow relative axial displacement between said coupling member and said connection portion; and wherein said first and second locking elements are displaceable in opposite directions along said transverse axis upon application of said lateral forces to transition said locking elements toward said unlocked position, and wherein said locking elements and said connection portion define engagement elements that cooperate with one another to substantially prevent said relative axial displacement between said coupling member and said connection portion; and wherein said connection portion defines at least one of said engagement elements along a length of said connection portion, each of said first and second locking elements including at least one of said engagement elements, said at least one of said engagement elements defined by said locking elements engaged with said at least one of said engagement elements defined by said connection portion when said locking elements are in said locked position to secure said connection member in a select axial position relative to said coupling member; and wherein said first locking element includes first and second locking portions, said second locking element including a third locking portion positioned intermediate said first and second locking portions and generally aligned with said first and second locking portions along said longitudinal axis.

4. The quick attachment apparatus of claim 3, wherein each of said locking elements defines a slot therethrough sized to receive said connection portion of the device, said slot having a slot length arranged generally along said transverse axis to allow transverse displacement of said locking elements relative to said connection portion to transition said locking elements between said locked and unlocked positions.

5. The quick attachment apparatus of claim 3, wherein said at least one of said engagement elements defined by said connection portion comprises a thread, and wherein said at least one of said engagement elements defined by said first and second locking elements comprises a thread segment.

6. The quick attachment apparatus of claim 3, wherein each of said first and second biasing members comprises a spring.

7. The quick attachment apparatus of claim 6, wherein at least a portion of each of said locking elements defines a groove, said spring at least partially positioned within said groove to maintain said spring in a substantially stationary axial position relative to a corresponding one of said locking elements.

8. The quick attachment apparatus of claim 6, wherein said spring comprises a canted coil spring.

9. The quick attachment apparatus of claim 3, wherein said first and second locking elements each include a push tab.

10. The quick attachment apparatus of claim 9, wherein said push tabs are arranged generally opposite one another on opposite sides of said longitudinal axis.

11. A quick attachment apparatus for use in association with orthopedic instrumentation or tools, comprising:

a connection portion of a device;

a coupling member defining a passage extending generally along a longitudinal axis and sized to receive said connection portion of the device, said connection portion defining a first thread; and a locking member associated with said coupling member, said locking member including first and second locking elements, each of said locking elements defining at least one thread segment engagable with said first thread, said locking elements transitionable between a locked position and an unlocked position, said first and second locking elements displaced in opposite directions along said transverse axis upon application of lateral forces to transition said locking elements toward said unlocked position, wherein said first locking element includes first and second locking portions, said second locking element including a third locking portion positioned intermediate said first and second locking portions and generally aligned with said first and second locking portions along said longitudinal axis;

a first biasing member engaged with said first locking element to bias said first locking element toward said locked position, and a second biasing member engaged with said second locking element to bias said second locking element toward said locked position; and wherein said first thread is disengaged from said thread segments of said locking elements when said locking elements are positioned in said unlocked position to allow variable adjustment of said connection portion to a select axial position relative to said coupling member; and wherein said first thread is engaged with said thread segments of said locking elements when said locking elements are positioned in said locked position to lock said connection portion in said select axial position relative to said coupling member; and wherein rotational displacement of said connection portion relative to said coupling member threadingly engages said first thread with said thread segments of said locking elements to provide relatively finer variable adjustment to said select axial position of said connection portion relative to said coupling member.

12. The quick attachment apparatus of claim 11, wherein said first thread comprises a substantially continuous thread formed along a length of said connection portion.

13. The quick attachment apparatus of claim 11, wherein each of said locking elements defines a slot therethrough sized to receive said connection portion of the device, said slot having a slot length arranged generally along a transverse axis and arranged transverse to said longitudinal axis to allow transverse displacement of said locking elements relative to said connection portion to transition said locking elements between said locked and unlocked positions.

14. The quick attachment apparatus of claim 13, wherein said thread segments of said locking elements are formed adjacent an end portion of said slot.

15. The quick attachment apparatus of claim 11, wherein each of said locking elements includes a push tab having a portion extending through a lateral opening in said coupling member, and wherein application of one of said lateral forces onto said push tab results in said displacement of a corresponding one of said locking elements generally along a transverse axis to transition said corresponding one of said locking elements to said unlocked position.

16. A quick attachment apparatus for use in association with orthopedic instrumentation or tools, comprising:

a connection portion of a device;

a coupling member defining a passage extending generally along a longitudinal axis and having an inner cross section sized to receive said connection portion of the device, said inner cross section of said passage including an inside surface;

a locking member associated with said coupling member, said locking member including first and second locking elements, each of said locking elements including a portion contained within said passage in said coupling member, each of said locking elements defining at least one thread segment engagable with said first thread, said locking elements transitionable between a locked position and an unlocked position, said first and second locking elements displaced in opposite directions along said transverse axis upon application of lateral forces to transition said locking elements toward said unlocked position;

a first biasing member engaged between said inside surface of said passage in said coupling member and said portion of said first locking element within said passage to bias said first locking element toward said locked position, and a second biasing member engaged between said inside surface of said passage in said coupling member and said portion of said second locking element within said passage to bias said second locking element toward said locked position, wherein each of said first and second biasing members comprises a spring, said spring being transitioned to a compressed state as a corresponding one of said locking elements is transitioned to said unlocked position upon application of said lateral force onto said corresponding one of said locking elements and exerts a biasing force onto said corresponding one of said locking elements to bias said corresponding one of said locking elements back toward said locked position; and wherein said first thread is disengaged from said thread segments of said locking elements when said locking elements are positioned in said unlocked position to allow variable adjustment of said connection portion to a select axial position relative to said coupling member; and wherein said first thread is engaged with said thread segments of said locking elements when said locking elements are positioned in said locked position to lock said connection portion in said select axial position relative to said coupling member; and wherein rotational displacement of said connection portion relative to said coupling member threadingly engages said first thread with said thread segments of said locking elements to provide relatively finer variable adjustment to said select axial position of said connection portion relative to said coupling member; and wherein said spring includes end portions that are interconnected with one another to define an annular ring extending about at least a portion of said corresponding one of said locking elements.

* * * * *